United States Patent [19]

Tagnon

[11] Patent Number: 4,572,629
[45] Date of Patent: Feb. 25, 1986

[54] APPARATUS FOR PRESENTATION OF EYE TESTS FOR TESTING NEAR AND DISTANT VISION

[75] Inventor: Luc Tagnon, Saint-Mande, France

[73] Assignee: Essilor International Cie Generale d'Optique, Paris, France

[21] Appl. No.: 441,248

[22] Filed: Nov. 12, 1982

[30] Foreign Application Priority Data

Nov. 13, 1981 [FR] France ............................... 81 21231

[51] Int. Cl.⁴ ............................................... A61B 3/02
[52] U.S. Cl. ..................................... 351/243; 351/239
[58] Field of Search ................................ 351/239, 243

[56] References Cited

U.S. PATENT DOCUMENTS

| | | | |
|---|---|---|---|
| 2,364,793 | 12/1944 | Jobe et al. | 88/20 |
| 3,012,472 | 12/1961 | Feinberg et al. | 88/20 |
| 4,298,253 | 11/1981 | Tagnon | 351/329 |

FOREIGN PATENT DOCUMENTS 944455  6/1956  Fed. Rep. of Germany .
1410284  8/1965  France .
2437818  4/1980  France .
2478459  9/1981  France .

Primary Examiner—Rodney B. Bovernick
Assistant Examiner—P. M. Dzierzynski
Attorney, Agent, or Firm—Charles E. Brown; Charles A. Brown

[57] ABSTRACT

Apparatus for displaying eyesight tests for patients comprising a viewing station a test support having a plurality of eyesight tests selectively visible from the viewing station along first and second optical paths, the first optical path being for near vision and devoid of optical focusing means and the second optical path being for far vision and having optical focusing means. The optical paths have a common section running from a selected test support panel. Each of the optical paths comprises a mirror for bending the viewing axis toward the viewing station, the mirror for the first optical path being rockably mounted or semireflecting for providing access to the second optical path.

16 Claims, 7 Drawing Figures

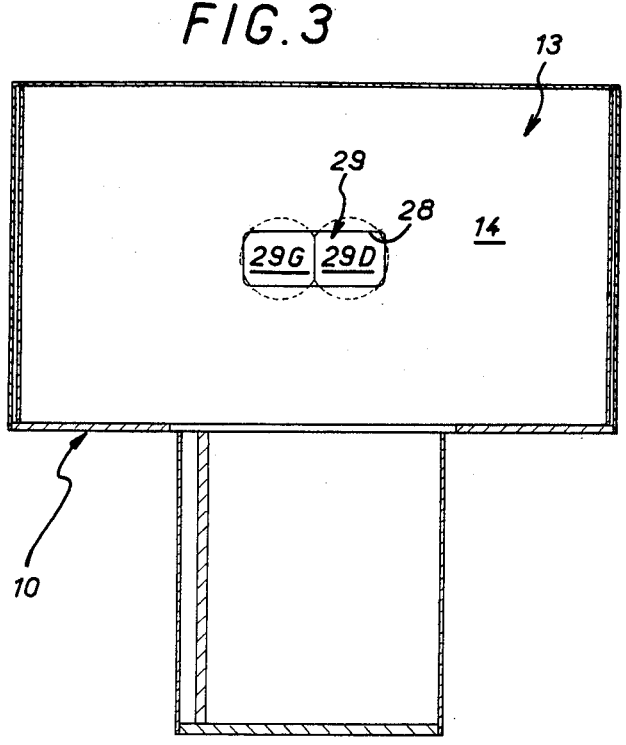
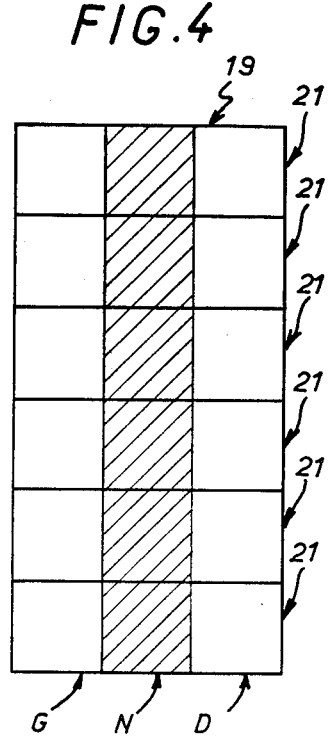
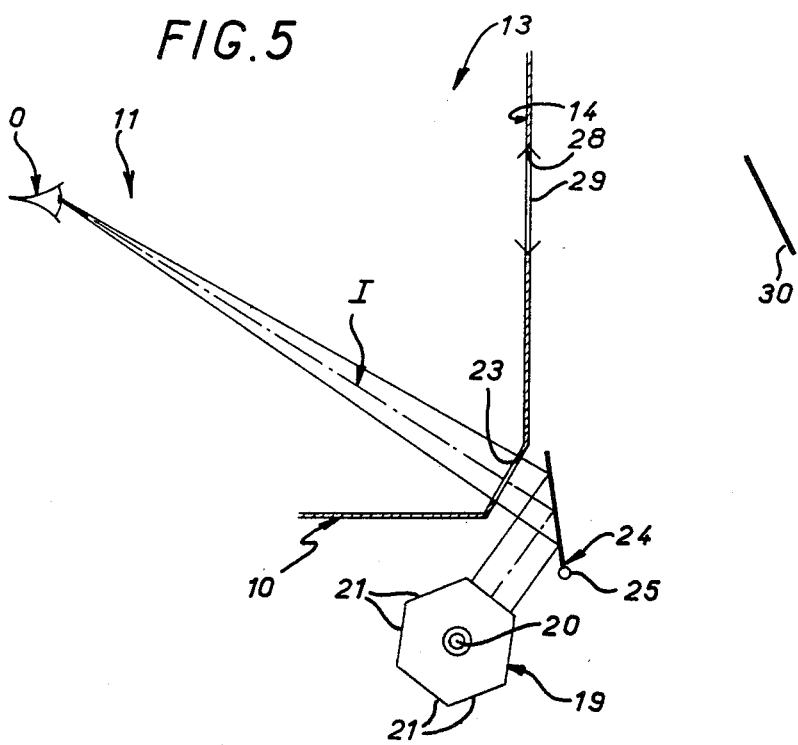

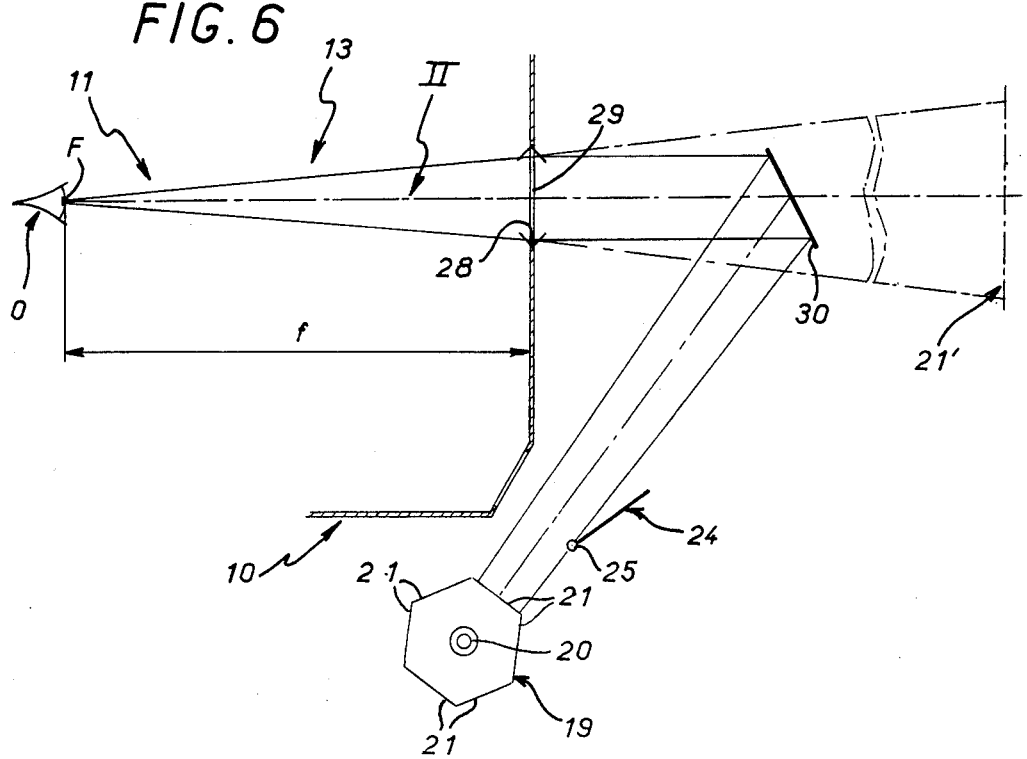
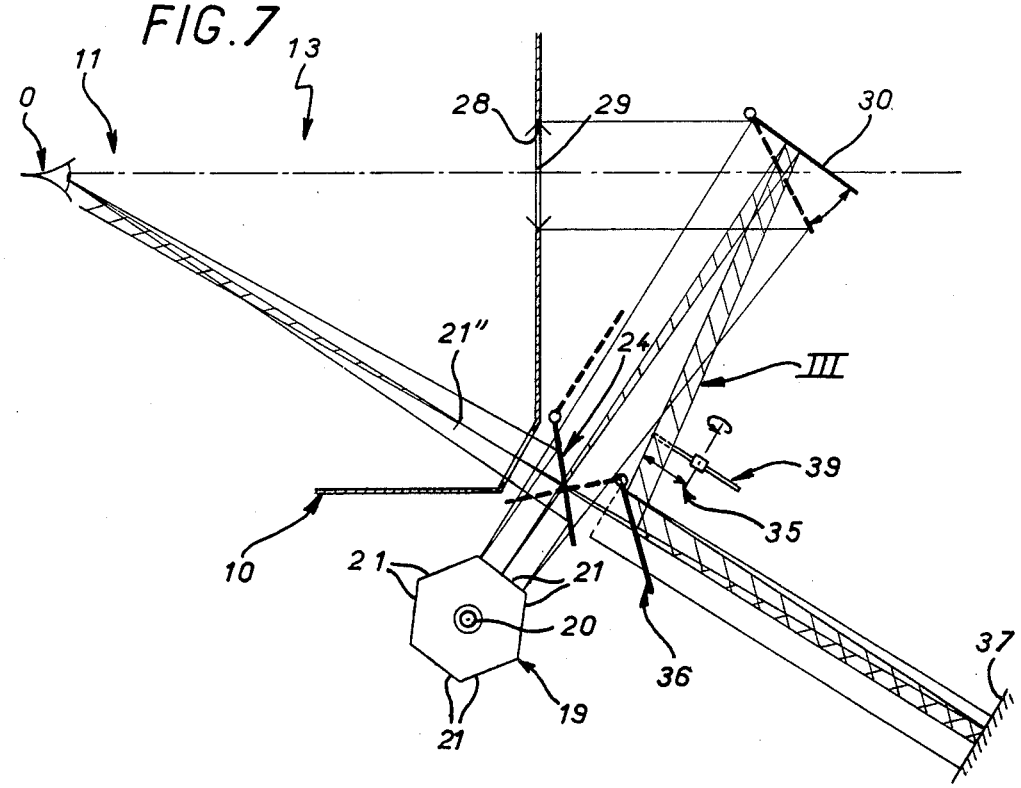

APPARATUS FOR PRESENTATION OF EYE TESTS FOR TESTING NEAR AND DISTANT VISION

FIELD OF THE INVENTION

The present invention relates generally to testing a patient's eyes and particularly to near vision and far vision testing, and more particularly to an eye testing apparatus.

SUMMARY OF THE INVENTION

According to the invention there is provided an apparatus for displaying eyesight tests for patients, said apparatus comprising a viewing station for the patient, a test support having a plurality of eyesight tests selectively visible from the viewing station along first and second optical paths, said first optical path being for near vision testing and being devoid of optical focusing means and said second optical path being for far vision testing and having optical focusing means.

The first optical path devoid of optical focusing means permits the patient to be tested to see the eyesight test directly and it is therefore adapted to test the near vision of the patient, the test support being located at a relatively short distance from the viewing station, between 0.40 and 0.90 meter, for example. The second optical path of the apparatus, according to the invention, comprising an optical focusing means permits the formation at a relatively long distance from the viewing station, of the order of, for example, 5 meters, a virtual image of the eyesight test on the test support, which is visible from the viewing station and therefore is adapted to test the far or distance vision of the patient.

Thus, the same apparatus of compact size can test the near and far vision of a patient without the patient having to move his head.

Further, such an apparatus provides a dual test by permitting the patient to view a single eyesight test or test object directly for near vision and through the focusing means for far vision, the corresponding optical paths advantageously, according to a feature of the invention, reach the same panel of the test support.

The testing of the patient's eyes is simplified and is not disturbed by a changing of the test object in switching from near vision testing to far vision testing and vice versa.

Preferably, according to the invention, the focal distance of the focusing means in the optical path for testing far vision is substantially equal to the length of the optical path for testing near vision and the image focal point of the focusing means is at the viewing station.

Owing to this arrangement the patient to be tested sees the test object at the same angle it is displayed or presented whether it is viewed for the far vision test or the near vision test. Accordingly, the patient's eyesight is tested independently of visual acuity.

Further, the far vision test object and the near vision test object can advantageously be formed by the same slide in this case.

In practice, according to a preferred embodiment of the invention, both optical paths of the apparatus, according to the invention comprise a mirror bending the optical axis toward the viewing station, at least the mirror for the near vision optical path being semireflecting or pivotally mounted to permit viewing of the eyesight test along the far vision optical path.

The compactness of the apparatus according to the invention is further enhanced since both optical axes are bent laterally and have a common section between the test support and the mirror of the near vision optical path.

According to a further aspect of the invention the mirror of the far vision optical path is pivotally mounted between two positions, and in the second position of the mirror there is associated a focusing means, a pivotally mounted or semireflecting mirror disposed obliquely relative to the near vision optical axis, and a return or reflecting mirror which is disposed perpendicular to the axis and is movably mounted along the axis.

This provides a third optical path for testing the near point of the patient thereby advantageously enlarging the field of use of the apparatus according to the invention.

Preferably, each of the optical paths comprising the same is double and a shutter is adapted to be interposed, at will, in the right part or the left part.

A one eye or monocular test is thus advantageously possible and as above, in the case of testing the near point of the patient it is advantageously unnecessary for the patient to move his head to test his right eye and his left eye.

In sum, the present eye testing apparatus provides in a very compact unit and permits an increased number of eye tests to be performed under the best conditions.

Further, the present eye testing apparatus utilizes simple mechanical means and is therefore reliable and dependable and the focusing means used along the optical axis or in the immediate vicinity thereof may advantageously be, technologically speaking, relatively rudimentary and therefore inexpensive.

PRIOR ART

To be sure, U.S. Pat. No. 3,012,472 discloses an eye testing apparatus for near and far visual tests comprising a single test support, in practice a rotatable drum, as in the apparatus according to the invention. But since the near visual tests and the far visual tests are different the test support stations are in turn distinct which for a given total number of eyesight tests available on the test support or the overall size thereof, reduces in half the total number of different tests.

Moreover, insofar as the near visual and far visual tests are different it is relatively difficult to provide a single viewing angle especially if, as in U.S. Pat. No. 3,012,472, different focal distances are envisaged for near and far vision.

It should also be emphasized that in U.S. Pat. No. 3,012,472, near vision of a test is through a viewer comprising focusing lenses, and not along an optical path devoid of focusing means as in the present eye testing apparatus, which viewer may interfere with the results.

Finally, since the near vision optical path is in practice straight in U.S. Pat. No. 3,012,472, the apparatus disclosed in that patent is not suitable for testing the near point contrary to the present invention.

These and other features and advantages of the invention will become apparent from the description which follows, given by way of example, with reference to the accompanying schematic drawings.

BRIEF DESCRIPTION OF THE DRAWINGS

FIG. 3 is another vertical sectional view taken broken line III—III in FIG. 1;

FIG. 4 is a view, laid out flat, of the test support of the eye testing apparatus;

FIG. 5 is a diagrammatic view corresponding to FIG. 1 illustrating a first mode of operation of the apparatus;

FIG. 6 is a similar diagrammatic view to FIG. 5 for a second mode of operation of the apparatus; and FIG. 7 is a diagrammatic view similar to FIGS. 5 and 6 for an alternative embodiment providing a third mode of operation of the apparatus.

DESCRIPTION OF THE PREFERRED EMBODIMENTS

Figure 1:
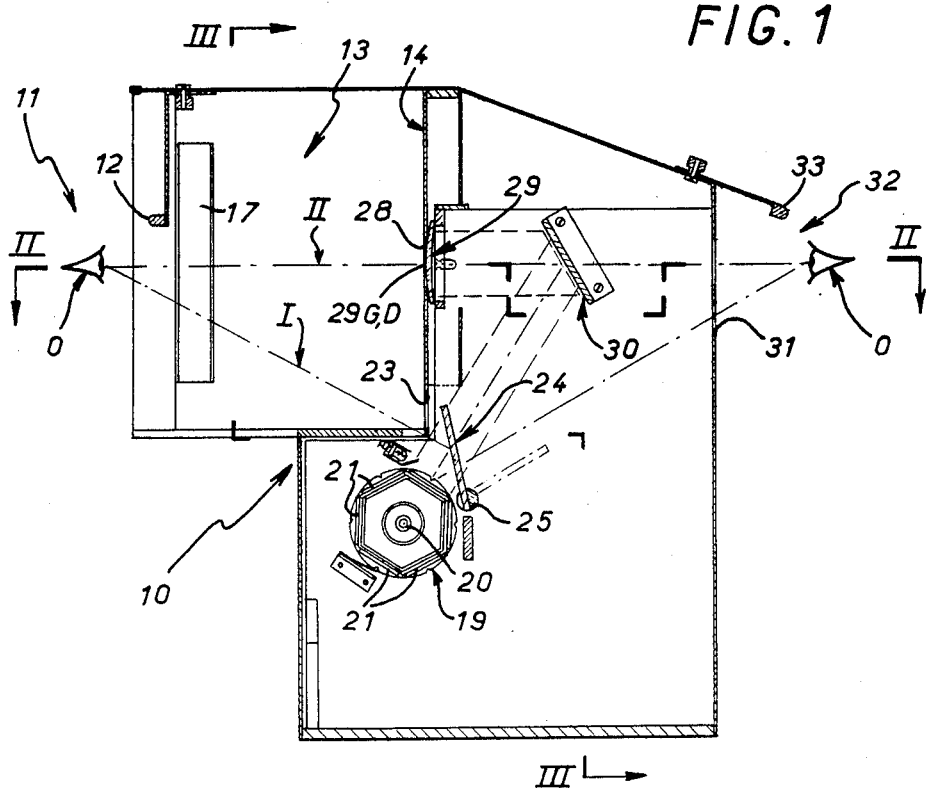
FIG. 1 is a vertical sectional view of the eye testing apparatus according to the invention, taken along I—I in FIG. 2.

As illustrated in the drawings the eye testing apparatus according to the invention generally comprises a housing defining an enclosure which will not be described in detail here since the details of its construction are within the ambit of those having ordinary skill in the art, and which is designated overall by reference 10.

Figure 2:
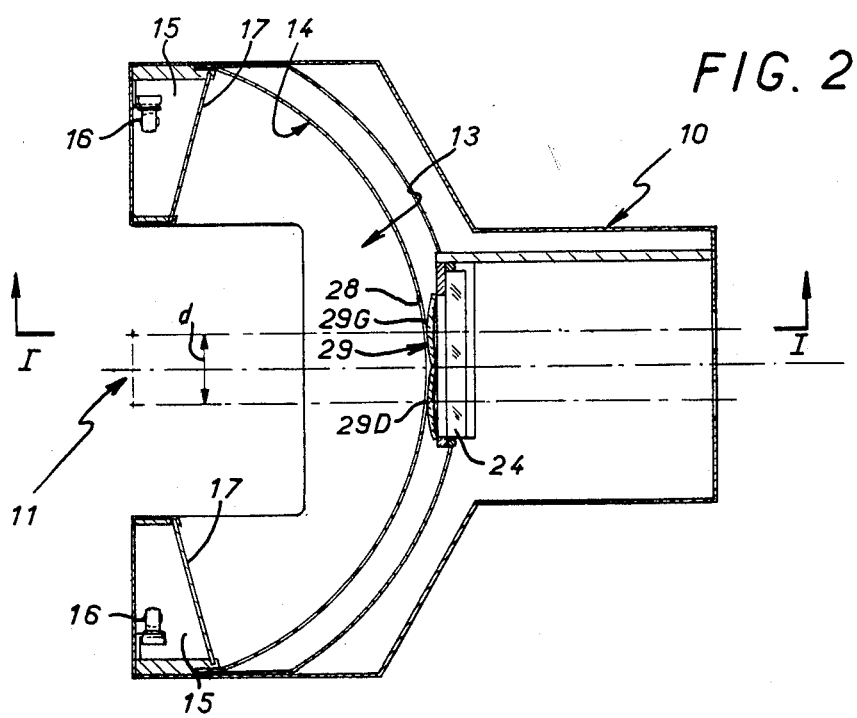
FIG. 2 is a horizontal sectional view of the eye testing apparatus taken along broken line II—II in FIG. 1.

A viewing station 11 is disposed at the front of the housing 10. In practice, the viewing station 11 essentially comprises a headrest 12 against which bears the forehead of the patient being tested. The headrest 12 is disposed along the axis of a chamber 13 which protrudes from the upper part and at the front of the housing 10 and which in plan view, as shown in FIG. 2, is generally crescent shaped. The endwall of the chamber 13 is formed by a cylindrical screen 14 or "cupola". Cavities 15 are formed at the lateral ends of the chamber 13 accommodating light sources 16, e.g., fluorescent lamps, and closed off by a translucid screen 17 which may have a pattern thereon.

Thus, for ergonomical eyesight testing, predetermined ambient lighting conditions may be provided which are known to have an influence on the visual performance of a person at a given work station.

In practice, in the illustrated arrangement and owing to the configuration of the cylindrical screen 14 of the chamber 13 the ambient lighting may advantageously cover a horizontal temple field of view equal to or greater than 60° and a vertical field of view greater than 60° to either side of the horizontal plane.

In the housing 10 is provided a single test support 19. In the illustrated embodiment the test support 19 is disposed in line with and slightly below the chamber 13 and comprises a drum of hexagonal section rotatably mounted on a horizontal shaft 20. In accordance with an arrangement which is also a matter within the ambit of ordinary skill in the art and not described in detail herein, the test support 19 is rotatably mounted for controlled intermittent movement between six different positions corresponding respectively to the display or presentation of one of the six lateral sides or panels 21 of the drum to the patient. Preferably, as shown in FIG. 4, each of the six panels 21 is divided into three substantially equal zones G, N and D. In practice for each panel 21 the zones G and D bear the same eyesight test or test object, zone G being for the left eye of the patient and zone D being for the right eye of the patient and zone N is devoid of eyesight tests. The test objects on each panel 21 of the test support 19 are different. The test objects are not illustrated in FIG. 4, but they may be of any usual type. Of course, for at least one of the panels 21 of the test support 21 zone G and/or zone D may be devoid of any eyesight test.

According to the invention, the test support 19 is visible from the viewing station 11 along either of two optical paths, of which a first optical path I has no optical focusing means and a second optical path II has an optical focusing means and is therefore suitable for testing the far vision of the patient.

In the illustrated embodiment the first optical path I extends downwardly from the viewing station 11 where the eye of the patient is schematically represented at O in FIGS. 1 and 5–7, and the first optical path I passes through orifice 23 in cylindrical screen 14 at the base thereof in the corresponding zone of chamber 13, this orifice 23 also extending along the bottom of the chamber 13.

The optical path I then reaches a mirror 24 which bends the optical path toward the viewing station 11. In the illustrated embodiment the mirror 24 is arranged spaced from and below the horizontal axis of the viewing station 11 and rockably mounted by a rotatable shaft 25 on which it is carried.

The second optical path II first extends horizontally from the viewing station 11 along the horizontal axis thereof. The second optical path II then passes through an orifice 28 in the middle area of the cylindrical screen 14. Behind the screen 14 is an optical focusing means 29 and then a mirror 30. In the illustrated embodiment the optical path II is double, the optical focusing means 29 comprising, side by side, two lenses 29G,29D the optical axes of which are spaced from each other a distance substantially equal to an average pupil spacing, symmetrically to the opposite sides of the horizontal axis of the viewing station 11.

In the embodiment illustrated in FIGS. 1–6 the mirror 30 is stationary. It bends the viewing axis from the test support 19 toward the viewing station 11.

Accordingly, both of the optical paths I,II comprise a mirror 24,30 bending the viewing axis toward the viewing station 11. The optical paths I and II have a common section between the test support 19 and the mirror 24 of optical path I and therefore starting from test support 19. Optical paths I and II therefore are directed to the same panel 21 of the test support 19.

Preferably, as shown, the viewing station 11, the focusing means 29 for optical path II and mirror 30 of the latter are disposed along the horizontal axis of the viewing station 11 and mirror 30 is semireflecting.

As shown in FIG. 1 there may be provided behind the semitransparent mirror 30 at the rear of the housing 10 which has an opening 31, an examining station 32 for the clinician or operator whose eye is schematically represented at O' in FIG. 1. The examining station 32 has a headrest 33 as shown. The mirror 24 is rockably mounted between two predetermined limit positions. In a first limit position of the mirror 24, as shown in solid line in FIG. 1, the patient at viewing station 11 may view the panel 21 of the test support 19 closest to him, as shown in FIG. 5. If the mirror 24 is not semireflecting, optical path II is then closed off. In any event for the second limit position, which is shown in chain-dotted line in FIG. 1, the retracted mirror 24 permits access to the second optical path II as shown in FIG. 6. The second optical path II then offers the patient at viewing station 11 along the horizontal axis a virtual image 21' of the preceding panel of the test support 19. Preferably, these arrangements are such that the viewing distance D of the test support 19 from the viewing station 11, including the bend in the viewing axis, is relatively short and corresponds to what is commonly referred to as near vision. It is preferably between 0.40 and 0.90 meter. Preferably, the arrangements are such that the viewing distance of the virtual image 21' from the viewing station is relatively long and corresponds to what is commonly called far vision. This distance is for example of the order of 5 meters.

Accordingly, the apparatus according to the invention advantageously permits the testing of the patient's eyesight for near vision and far vision with the same test object.

For the testing of at least the far vision of the patient the operator has an examining station 32 permitting direct viewing of the test support 19 for monitoring the test object presented to the patient for checking the patient's verbal responses.

Zone N on each side 21 of the test support 21 may be used to carry any legend useful for the operator. A similar possibility exists for testing the patient near vision when the mirror 24 is semireflecting rather than rockably mounted.

Preferably, the arrangements are such that the focal distance f of the focusing means 29 for optical path II for testing far vision is substantially equal to the length of the optical path I for testing near vision, defined by the viewing distance D of the test support 10 from the viewing station 11 and the focal image F' of the focusing means 29 is at the viewing station 11 along the horizontal axis at the location of the eye O of the patient being tested. Thus, advantageously the patient views at the same angle the panel 21 of the test support 19 he views directly as the virtual image 21' which is viewed through the focusing means 29. The eye testing offered by the apparatus is therefore advantageously independent of the patient's acuity.

It should be noted that in the drawings which are diagrammatic the preceding arrangements are not respected since the distance D is longer than distance f. To respect the same the viewing station 11 must be moved closer to the test support 19 or the viewing station must be moved farther from the focusing means 29.

In the embodiment illustrated diagrammatically in FIG. 7, the mirror 30 in the second optical path II for far vision testing is also rockably mounted between two positions, one shown in chain-dotted line in FIG. 7, for far vision testing, and the other in solid line in FIG. 7, for testing the near point of the patient.

In the solid line position there is associated with the mirror 30 a focusing means 35, a semireflecting mirror 36 disposed along the continuation of the near viewing axis, obliquely with respect to the latter and in the direction away from the viewing station 11, and a return or reflecting mirror 37 disposed perpendicular to the continuation of the axis and adjustably mounted therealong.

Thus, a third optical path III is provided which starting from the test support 19 is bent successively by mirrors 30 and 36 before being directed by the mirror 37 to the viewing station 11 as diagrammatically shown by hatching in FIG. 7. Obviously, in this case, the mirror 24 in the first optical path I is pivotally mounted so as not to interfere with the third optical path III.

Preferably, the first optical path III is a double optical path, the focusing means 35 thereof being provided with two lenses disposed side by side in the same plane. As illustrated, the focusing means is associated with a shutter 39 adapted to be interposed at will in the right part or the left part for monocular testing of the vision of the patient.

In any event, after reflection by the mirrors 30,36 and 37, the focusing means 35 provides an image 21" of panel 21 of the test support 19 to the patient disposed along the near vision optical axis or optical path I.

By displacing mirror 37 along optical path I it is possible, at will, to bring the image 21" closer or farther from the viewing station, in a range of distance compatible with the measurement of the near point of the patient.

Obviously the present invention is not intended to be limited to the illustrated and described embodiments but on the contrary admits of various alternatives and modifications, which will be apparent to those skilled in the art, without departing from the spirit and scope of the invention.

In particular it is possible to provide a single zone on each side 21 of the test support 19 instead of three zones, in which case conventional arrangements may be adapted employing, for example, prisms, for superimposing in the zone the two right-left parts for each optical path involved. Also, the cupola the chamber 13 forms may be utilized for other tests than those described above and/or the superposition of such other test thereon.

What is claimed is:

1. Apparatus for displaying eyesight test objects for patients, said apparatus comprising a viewing station for the patient, a test support having a plurality of eyesight test objects, said eyesight test objects being selectively positionable at a single display station, a single selected one of said eyesight test objects positioned at said single display station being visible from the viewing station along each of first and second optical paths, said first optical path being for near vision testing and being devoid of optical focusing means and said second optical path being for far vision testing and having optical focusing means.

2. Apparatus according to claim 1, wherein said test support comprises a plurality of panels carrying said eyesight test objects, said test support panels being selectively positionable at said single display station for viewing in a selected position along each of said first and second optical paths.

3. Apparatus according to claim 2, wherein said two optical paths have a common section running from the selected test support panel.

4. Apparatus according to claim 1, wherein the focal distance of said focusing means in said second optical path is substantially equal to length of said first optical path and the image focal point of said focusing means being at the viewing station.

5. Apparatus according to claim 1, wherein each of said first and second optical paths comprises a mirror for bending the viewing axis toward said viewing station, the mirror for said first optical path being rockably mounted.

6. Apparatus according to claim 1, wherein each of said first and second optical paths comprises a mirror for bending the viewing axis toward said viewing station, the mirror for said first optical path being semireflecting.

7. Apparatus according to claim 1, wherein each of said first and second optical paths comprises a mirror for bending the viewing axis toward said viewing station, the mirror for said first optical path being selectively operable for providing access to said test support along said second optical path.

8. Apparatus according to claim 7, wherein said focusing means lying along said second optical path is aligned along a horizontal axis with said viewing station, and the mirror for said first optical path is spaced below said horizontal axis.

9. Apparatus according to claim 7, wherein said mirror for said second optical path is semitransparent, an examining station for an operator being provided to the side of said semitransparent mirror remote from said viewing station.

10. Apparatus according to claim 7, wherein said mirror of said second optical path is rockably mounted between a first position for far vision testing and a second position for near point testing, a focusing means and a semireflecting mirror being disposed along an oblique continuation of said first optical path away from said viewing station, and a return mirror being disposed perpendicular to said continuation of said first optical path and adjustably mounted along said continuation.

11. Apparatus according to claim 1, wherein at least one of said first and second optical paths is double, and associated with a shutter adapted to be selectively interposed in the right and left part of the related optical path for monocular testing.

12. Apparatus according to claim 1, further comprising lighting means for providing predetermined ambient lighting conditions.

13. Apparatus according to claim 12, wherein said lighting means are disposed in a chamber having a cylindrical endwall along the viewing axis of the apparatus so that the ambient lighting covers a horizontal field of view equal to or greater than 60° and a vertical field of view greater than 60° to each side of a horizontal plane.

14. Apparatus for displaying eyesight test objects for patients, said apparatus comprising a viewing station for the patient, a test support supporting an eyesight test object at a single display station with said eyesight test object being at a single position selectively visible from said viewing station along each of first and second optical paths, said first optical path being for near vision testing and being devoid of optical focusing means and said second optical path being for far vision testing and having optical focusing means.

15. Apparatus according to claim 14, wherein said test support comprises a plurality of panels carrying a plurality of said eyesight test objects, said test support panels being selectively positionable at said single display station for selective viewing along both said first and second optical paths.

16. Apparatus according to claim 15, wherein said two optical paths have a common section running from the selected test support panel at said display position.

* * * * *